US010308578B2

(12) United States Patent
Messenger

(10) Patent No.: US 10,308,578 B2
(45) Date of Patent: *Jun. 4, 2019

(54) SYSTEM AND PROCESS FOR REMOVAL OF ORGANIC CARBOXYLATES FROM MONO ETHYLENE GLYCOL (MEG) WATER STREAMS BY ACIDIFICATION AND VAPORATION UNDER VACUUM

(71) Applicant: Cameron Solutions, Inc., Houston, TX (US)

(72) Inventor: Brian E. Messenger, Hook (GB)

(73) Assignee: CAMERON SOLUTIONS, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/017,530

(22) Filed: Jun. 25, 2018

(65) Prior Publication Data

US 2018/0305282 A1 Oct. 25, 2018

Related U.S. Application Data

(60) Continuation of application No. 15/044,752, filed on Feb. 16, 2016, now Pat. No. 10,005,708, which is a
(Continued)

(51) Int. Cl.
C07C 29/88 (2006.01)
B01D 3/00 (2006.01)
(Continued)

(52) U.S. Cl.
CPC ............ C07C 29/88 (2013.01); B01D 3/009 (2013.01); C07C 29/50 (2013.01); C07C 29/76 (2013.01);
(Continued)

(58) Field of Classification Search
CPC .................................................... C07C 29/88
See application file for complete search history.

(56) References Cited

U.S. PATENT DOCUMENTS 2,788,373 A 4/1957 Mills, Jr. et al.
4,822,926 A 4/1989 Dye
(Continued)

FOREIGN PATENT DOCUMENTS

WO 2007073204 A1 6/2007
WO 2009017971 A1 2/2009
(Continued)

OTHER PUBLICATIONS

EPO, "European Examination Search Report from corresponding European Application No. 14188167.2, Cameron Solutions, Inc.", Jun. 9, 2017, Publisher: EPO.
(Continued)

Primary Examiner — Medhanit W Bahta
(74) Attorney, Agent, or Firm — Hauptman Ham, LLP

(57) ABSTRACT

A system and method for removing organic carboxylates from a mono ethylene glycol ("MEG") stream includes a reaction vessel; means for cooling and diluting the MEG stream being routed to the reaction vessel; means for acidifying the cooled and diluted MEG stream during its residence time within the reaction vessel; and means for removing an acetic-rich overhead stream from the reaction vessel. The acidification of the cooled and diluted MEG stream occurs under a vacuum. The reaction vessel may be located downstream of a calcium removal vessel and receive a filtered bottom stream from that vessel, or it may be a single reaction vessel that cycles between a calcium removal mode and an acetate removal mode, with the pressure of the single vessel being greater during the calcium removal mode than during the acetate removal mode.

28 Claims, 7 Drawing Sheets

Related U.S. Application Data division of application No. 14/051,138, filed on Oct. 10, 2013, now abandoned.

(51) Int. Cl.
*C07C 29/50* (2006.01)
*C10L 3/10* (2006.01)
*C07C 29/76* (2006.01)
*C07C 29/78* (2006.01)

(52) U.S. Cl.
CPC .............. *C07C 29/78* (2013.01); *C10L 3/107* (2013.01); *C10L 2290/12* (2013.01); *C10L 2290/54* (2013.01)

(56) References Cited

U.S. PATENT DOCUMENTS

| | | |
|---|---|---|
| 6,184,423 B1 | 2/2001 | Jen |
| 6,525,229 B2 | 2/2003 | Baars et al. |
| 2005/0072663 A1 | 4/2005 | Laborie et al. |
| 2008/0182999 A1 | 7/2008 | Rekers et al. |

FOREIGN PATENT DOCUMENTS

| | | |
|---|---|---|
| WO | 2010080038 A1 | 7/2010 |
| WO | 2012171554 A1 | 12/2012 |
| WO | 2013074183 A1 | 5/2013 |
| WO | 2013168077 A1 | 11/2013 |

OTHER PUBLICATIONS

EPO, "Search Report for Application No. 14188167.2", dated Sep. 20, 2018.

SYSTEM AND PROCESS FOR REMOVAL OF ORGANIC CARBOXYLATES FROM MONO ETHYLENE GLYCOL (MEG) WATER STREAMS BY ACIDIFICATION AND VAPORATION UNDER VACUUM

CROSS-REFERENCE TO RELATED APPLICATIONS

This application is a continuation application which claims priority to U.S. patent application Ser. No. 15/044,752, filed Feb. 16, 2016, which was a divisional application which claimed priority to U.S. patent application Ser. No. 14/051,138 filed on Oct. 10, 2013, both of which are incorporated herein by reference.

BACKGROUND OF THE INVENTION

This invention relates to systems and methods designed to treat mono ethylene glycol ("MEG") streams used in the oil and gas industry to control hydrates formation in the production pipeline. More particularly, the invention relates to systems and processes which allow for removal of carboxylates from the MEG water stream of a MEG reclamation and regeneration package to reduce MEG losses.

In the oil and gas industry, dry (lean) MEG is injected into the production pipeline to control the formation of hydrates within the produced stream. The MEG injection is part of a MEG loop of a gas production facility. The loop typically includes a reclamation and regeneration package to treat the wet (rich) MEG and reclaim as much MEG as possible for reinjection into the pipeline.

The formation waters and condensed waters, which arrive at the gas production facility along with the raw hydrocarbon products, contain organic acids. Because these organic acids are highly soluble in MEG-water mixtures, they tend to follow the MEG-water stream. Additionally, in order to protect production pipelines against corrosion, and to remove dissolved divalent cations from the MEG stream, the pH of the MEG-water in the pipeline is elevated by the addition of bases such as sodium hydroxide. At elevated pH, the organic acids are present as a carboxylate salt (e.g., sodium acetate).

The low volatility of the carboxylate salts results in their accumulation in MEG process streams within the MEG loop. This accumulation, in turn, results in increased viscosity and density, making the MEG streams more difficult to pump.

To control the carboxylate levels in the MEG loop, the carboxylate-rich MEG is periodically discharged. However, this results in loss of MEG from the system and requires replacement to ensure the MEG inventory of the loop is maintained. Therefore, a need exists for systems and processes which control the carboxylate levels and reduce or eliminate MEG loss in the loop.

Carboxylate accumulation (either as the organic acid or as the corresponding salt) is an issue for MEG reclamation and regeneration packages due to the high solubility of these species in the water-MEG aqueous phase.

In order to minimize corrosion issues, the MEG Loop is operated at relatively high pH whereby the carboxylic acids are present predominantly as the carboxylate salts which have low volatility and, thus, are not removed in the overheads (produced water) stream from the regenerators or reclaimers of the MEG Recovery Package. Their high solubility in alkaline MEG solutions means that they do not precipitate when the pH is raised to remove the calcium, magnesium and other divalent cations.

Accumulation of acetates can lead to elevated density and viscosity in MEG streams which, in turn, lead to operational difficulties. Therefore, a need exists for a system and process to remove organic carboxylates from the MEG water stream.

SUMMARY OF THE INVENTION

By employing a system and process made and practiced according to this invention, the problems discussed in the above background section are minimized because the acetate levels are controlled to a manageable level while MEG losses associated with the acetate removal process are kept to a minimum when compared to the alternative.

A system and process for removing organic carboxylates from a mono ethylene glycol ("MEG") stream includes a reaction vessel; means for cooling and diluting the MEG stream being routed to the reaction vessel; means for acidifying the cooled and diluted MEG stream during its residence time within the reaction vessel; and means for removing an acetate-rich overhead stream from the reaction vessel. The acidification of the cooled and diluted MEG stream occurs under a vacuum.

The reaction vessel may be located downstream of a calcium removal vessel and receive a filtered bottom stream from that vessel, or it may be a single reaction vessel that cycles between a calcium removal mode and an acetate removal mode, with the pressure of the single vessel being greater during the calcium removal mode than during the acetate removal mode.

Preferably, the cooling and diluting means results in the incoming MEG stream to be 50 wt % MEG at a temperature in a range of 80° to 100° C. In the acetate removal mode, the pressure is sub-atmospheric, preferably in a range of 0.1 to 0.3 bar. The acidifying means, which may be hydrochloric acid, results in the cooled and diluted MEG stream during its residence time within the reaction vessel to have a pH in a range of 3.5 to 5.5.

Objects of the invention include providing a system and process which: (1) can be retrofitted into existing MEG loops; (2) controls and reduces the amount of acetates in the MEG water stream; (3) extends the length of the production run; (4) reduces MEG loss; and (5) increases MEG recovery for re-use.

BRIEF DESCRIPTION OF THE DRAWINGS

FIG. 3 is a graph of acetate removal as a function of temperature and pressure.

FIG. 4 is a graph of MEG losses in the reaction vessel overheads as a function of temperature and pressure.

FIG. 5 is a graph of acetate removal against MEG loss for three temperatures (80, 90 and 100° C.).

FIG. 6 is a graph of calculated MEG loss per kg of acetate rejected as a function of operating pressure.

FIG. 7 is a graph of calculated acetate removed from the reaction vessel as a function of initial pH (3.5, 4.5, 5.5), temperature (60-100° C.), and operating pressure (0.1-0.3 bara).

ELEMENTS AND ELEMENT NUMBERING USED IN THE DRAWING FIGURES

Figure 1A:
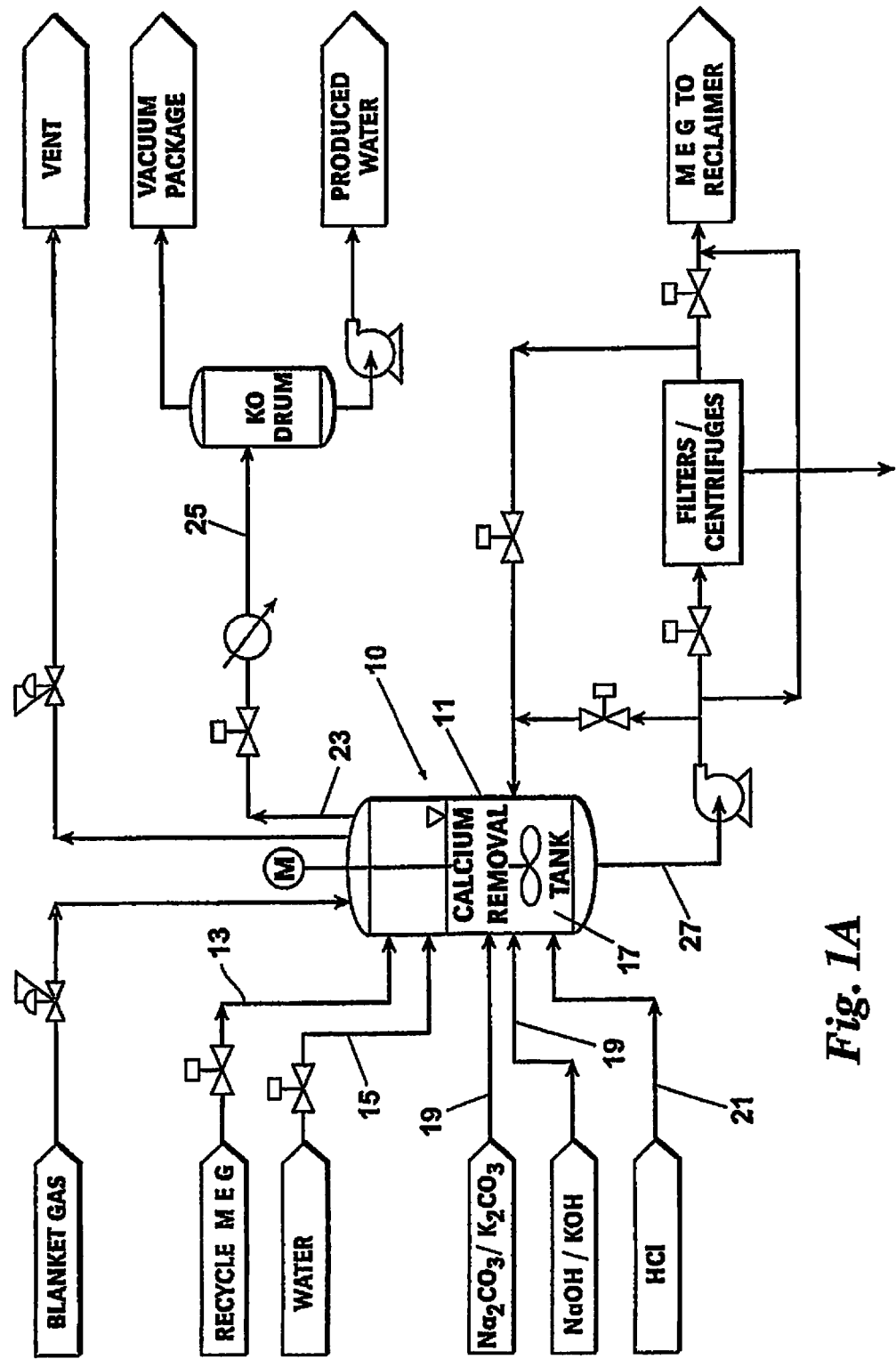
FIG. 1A is a preferred embodiment of a system and process practiced according to this invention. A single reaction vessel is used for the removal of calcium and carboxylates from a mono ethylene (MEG) water stream. The reaction vessel swings or cycles between those two removal modes. The acetate-rich overhead stream is routed directly to a knock-out drum.

10 System
11 Reaction vessel
13 Incoming carboxylates-rich MEG stream
15 Water stream
17 Cooled and diluted MEG water stream
19 Precipitating means
21 Acidifying means
23 Acetate-rich overhead stream
25 Condensed acetate-rich overhead stream
27 Calcium carbonates bottoms stream
29 Filtered calcium carbonates bottoms stream
101 Reactor vessel
102 pH probe
103 Dissolved oxygen probe
104 Redox probe
105 Electrical conductivity probe
106 Stirrer
107 Hot oil circulator bath and heater
108 Condenser
109 Distillate collection vessel
110 Vacuum pump
111 Pressure control valve
112 Pressure transducer
113 Oxygen-free nitrogen supply

DETAILED DESCRIPTION OF THE PREFERRED EMBODIMENTS

A system and process made and practiced according to this invention allows a target salt (in this case acetate) to accumulate in a reaction vessel and then removes the acetate from a concentrated liquor within the reaction vessel, thereby keeping vessel site and inventory to a minimum.

Referring to the drawings and first to FIGS. 1A and B, a system 10 for removing organic carboxylates like acetates from a MEG water stream includes a reaction vessel 11 as part of the MEG loop of a MEG reclamation and regeneration package. The MEG reclamation unit (not shown) is typically operated at a temperature in a range of about 120°-140° C. and at sub-atmospheric pressure (about 0.1-0.3 bara). The recycle loop within the reclamation unit is operated at elevated pressure (about 4 bar). The reaction vessel 11 is closely coupled to the recycle loop of the package.

The incoming carboxylate-rich MEG stream 13 is typically at 80-90 wt % MEG and high ph (>9.5). The incoming MEG stream 13 is cooled and diluted with water 15 to yield a cooled and diluted MEG water stream 17 which enters and resides within reaction vessel 11 as a MEG water mixture. The cooled and diluted MEG stream 17 is preferably at a temperature of about 80-100° C. and 50 wt % MEG.

The reaction vessel 11 can be switched between a calcium removal mode (high pH, atmospheric pressure) and an acetate removal mode (low pH, sub-ambient pressure). The frequency of calcium removal cycles and acetate removal cycles can be varied to control the levels of calcium and organic acids in the MEG loop depending on the composition of the MEG feed entering the MEG regeneration package.

When reaction vessel 11 is in a calcium removal mode or cycle, the vessel 11 operates at atmospheric pressure and removes calcium and other divalent cations from the incoming MEG water stream by elevating pH. Precipitating means 19 such as sodium or potassium carbonate or sodium or potassium hydroxide are introduced to the reaction vessel 11. Salts residing in the MEG water mixture—such as calcium chloride and, commonly, lesser amounts of other divalent salts like magnesium, barium and strontium chlorides—react with the precipitant agent and precipitate out of the MEG water mixture as solid crystals. The solid crystals are removed as a bottom stream 27.

When reaction vessel 11 is in an acetate removal mode, the vessel 11 operates under a vacuum (preferably in a range of about 0.1-0.3 bar) and removes carboxylates by lowering pH (preferably in a range of about 3.5-5.5). The stream 17 is acidified within the reaction vessel 11 using acidifying means 21 such as hydrochloric acid (e.g., 30 w % HCl in water) to achieve a pH in a range of about 3.5-5.5. The pressure in reaction vessel 11 is then reduced to 0.1-0.3 bar and acetates are evolved along with water, some carbon dioxide and some MEG. Means well known in the art are employed to remove the acetate-rich overhead stream 23 from the vessel 11.

Figure 3:
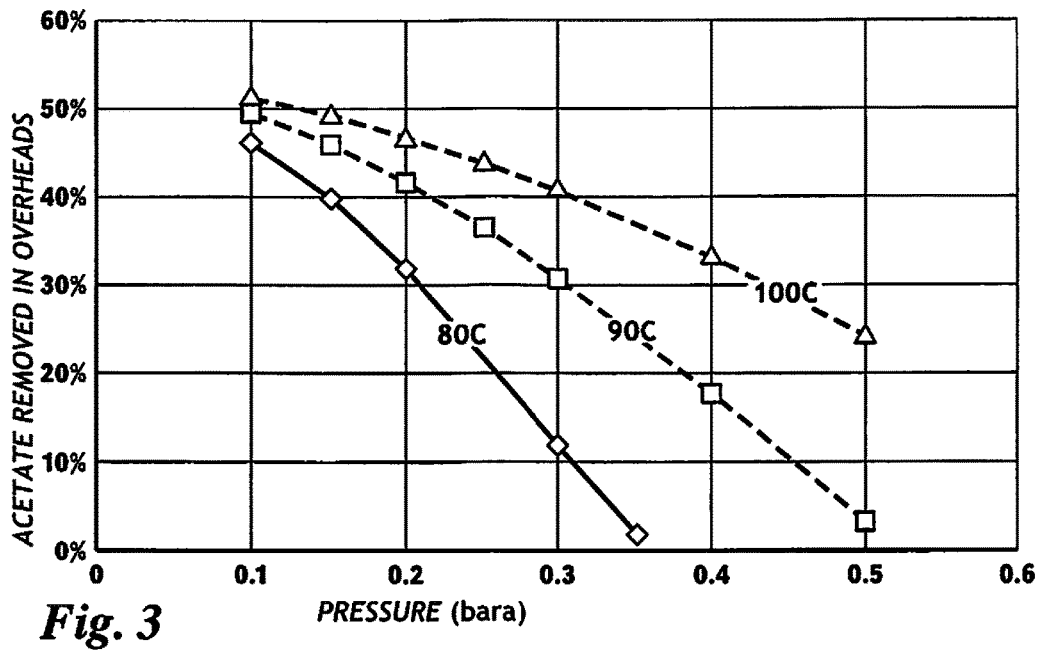
FIGS. 3 to 7 show simulated results of a system and process made according to FIGS. 1A, 1B and 2 for acetate removal from a model solution where solution pH was reduced to 4.5 prior to raising temperature and reducing pressure.
Figure 4:
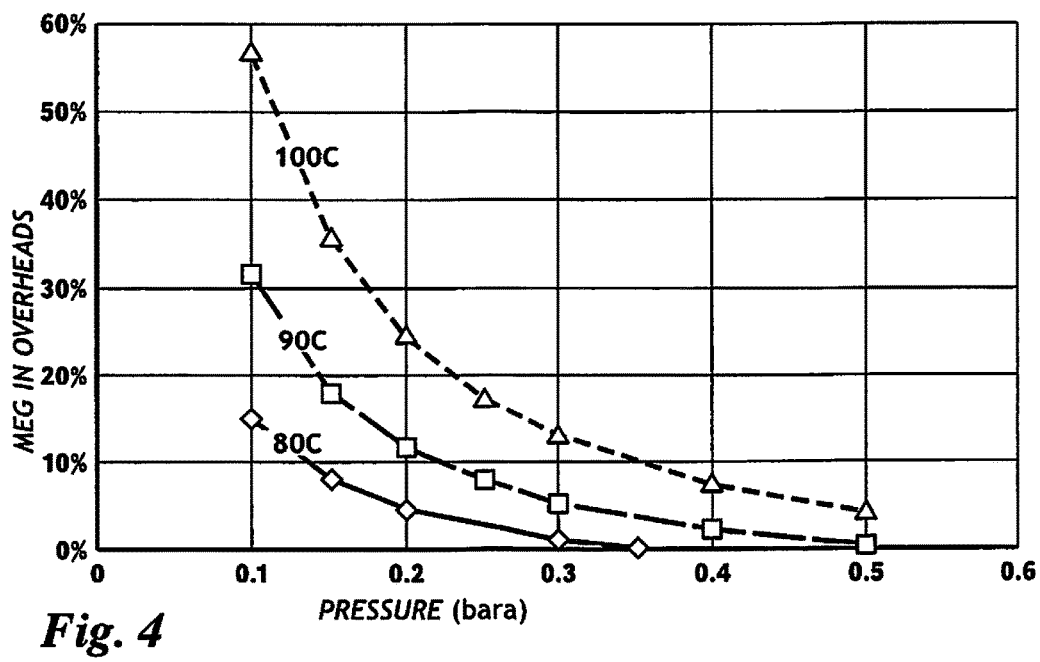

The composition of the overhead stream 23 from the reaction vessel 11 is primarily a function of temperature and pressure (see FIGS. 3 & 4). Ideally, the overhead stream 23 contains the maximum quantity of acetic acid and a minimum quantity of MEG. The results reported below in FIGS. 3 & 4 can be applied to determine an optimum initial pH, temperature and pressure regime whereby the maximum yield of acetic acid is combined with a reduced yield of MEG in the stream 23.

Figure 1B:
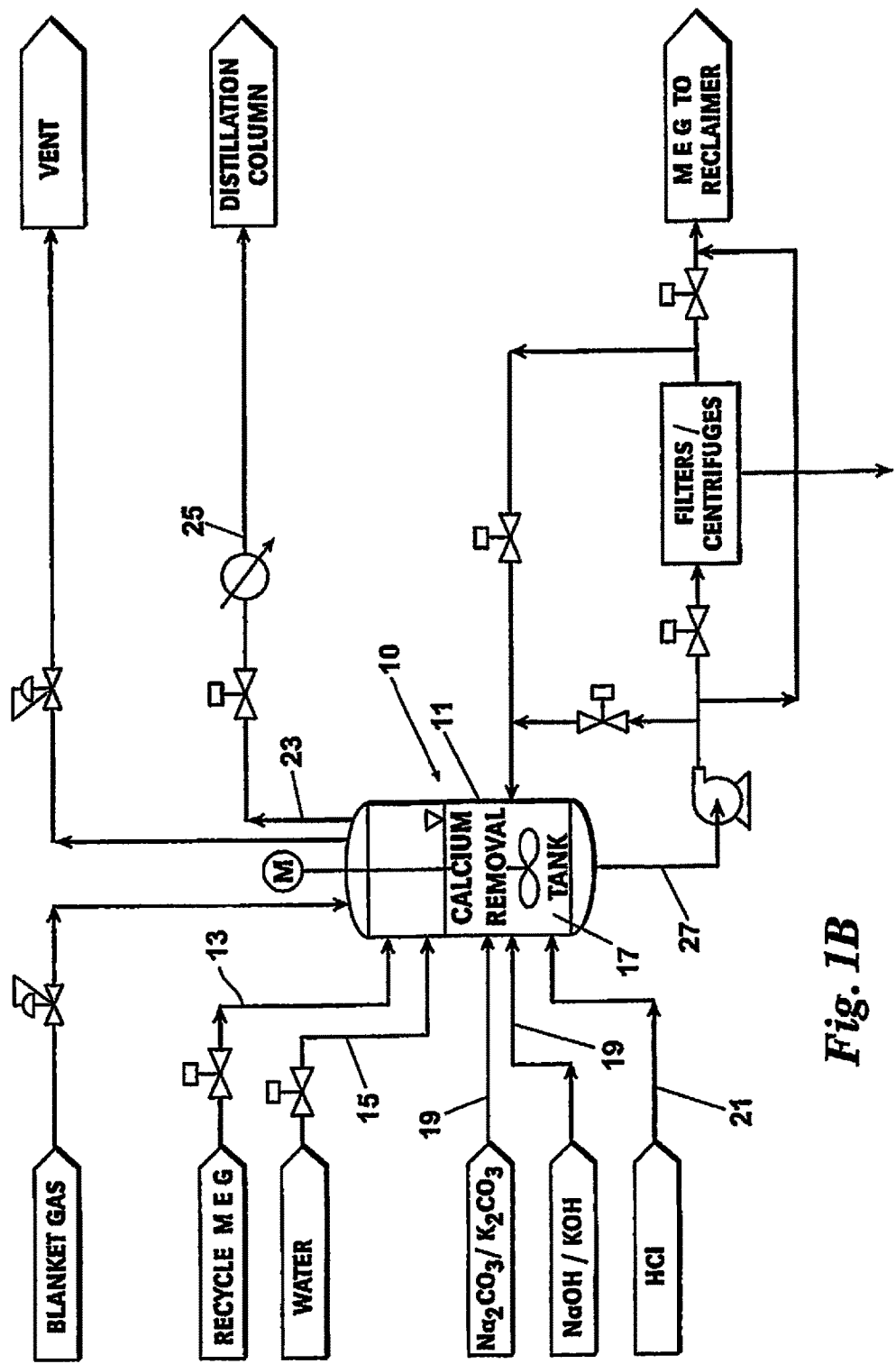
FIG. 1B is another preferred embodiment of a system and process practiced according to this invention. A single reaction vessel is used for the removal of calcium and carboxylates from a mono ethylene (MEG) water stream. Similar to FIG. 1A, the vessel cycles between those two removal modes. The acetate-rich overhead stream is routed directly to a distillation column where it is mixed with a MEG-water overhead stream from a reclaimer.

In the system of FIG. 1A, the overhead stream 23 is condensed and the condensed stream 25 (low pH<3) may be routed to water treatment equipment or neutralized in a knock-out drum. In the system of FIG. 1B, the overhead stream 23 is condensed and the condense stream 25 is routed directly to the distillation column where it is mixed with a MEG-water overhead stream from the reclaimer. The acetates partition between the aqueous phase (produced water) and the lean MEG phase. Routine experimentation can be used to determine the partitioning of acetic acid between water and lean MEG to determine the preferred routing of acetic acid-MEG-water stream from the acetate removal process.

Figure 2:
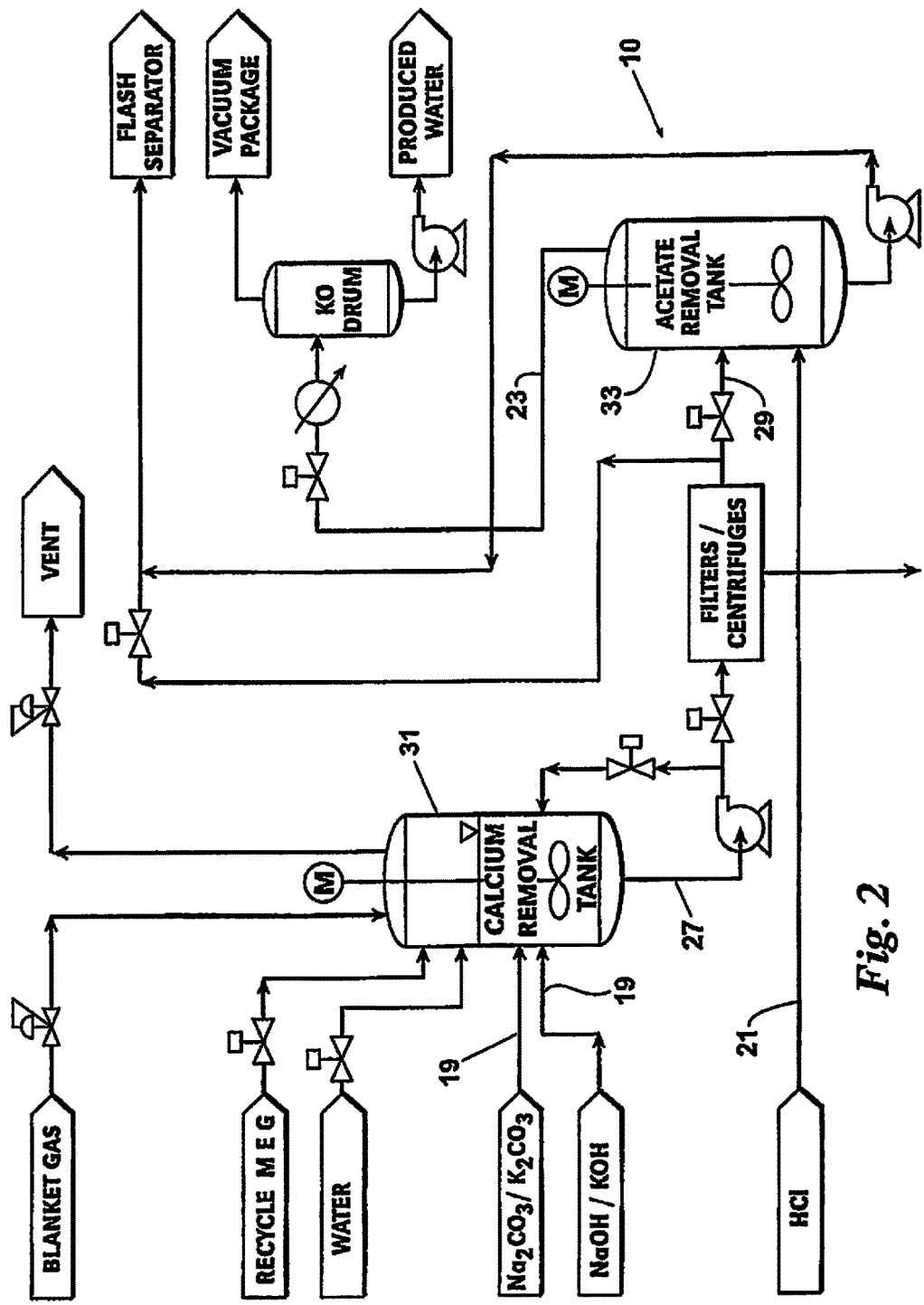
FIG. 2 is yet another preferred embodiment of a system and process practiced according to this invention. One reaction vessel is used for the removal of calcium from the MEG-water stream and another reaction vessel is used for the removal of carboxylates. The high pH stream generated in the calcium removal vessel is filtered to remove solids and then treated with hydrochloric acid in the acetate removal vessel operated at sub-atmospheric pressure.

Referring now to FIG. 2, separate vessels 31, 33 are used for calcium removal and carboxylates removal, respectively.

During simultaneous production of calcium and carboxylic acids the calcium (and other divalent cations) are precipitated in vessel 31 at approximately 80° C. and 1.0 bar by raising the pH using precipitating means 19 and filtering the resulting calcium carbonates stream 27. The centrate/filtrate steam 29 is acidified using acidifying means 21 at 80-100° C. and at sub-atmospheric pressure (about 0.1 to 0.3 bar) in vessel 33 to remove the organic acids and water as an overhead stream 23. The calcium-free and organic acid-free MEG can be returned to the production process.

However, the same calcium removal process as that described for vessel 11 (see FIGS. 1A and 1B) is employed within vessel 31, as is the same acetate removal process for vessel 33.

Simulated Results

Simulated results were obtained employing OLI STREAM ANALYZER™ software (OLI Systems, Inc., Cedar Knolls, N.J. A model feed representing a high pH, 50% MEG solution with 3 wt % dissolved sodium acetate and excess sodium hydroxide and sodium bicarbonate was reacted with hydrochloric acid (as HCl) to reduce the pH to 3.5-5.5. The temperature of the solution and the reaction pressure were adjusted and the composition of the predicted overhead stream was calculated. The acetate content of the reaction mixture was fixed at 30 kg sodium acetate.

FIG. 3 shows acetate removed as a function of temperature and pressure. The highest levels of acetate are removed at elevated temperature and low pressure. FIG. 4 shows that MEG losses are highest at elevated temperature and reduced pressure. Therefore, an optimum temperature/pressure condition is required to maximize acetate removal while reducing or minimizing MEG losses to acceptable levels.

Figure 5:
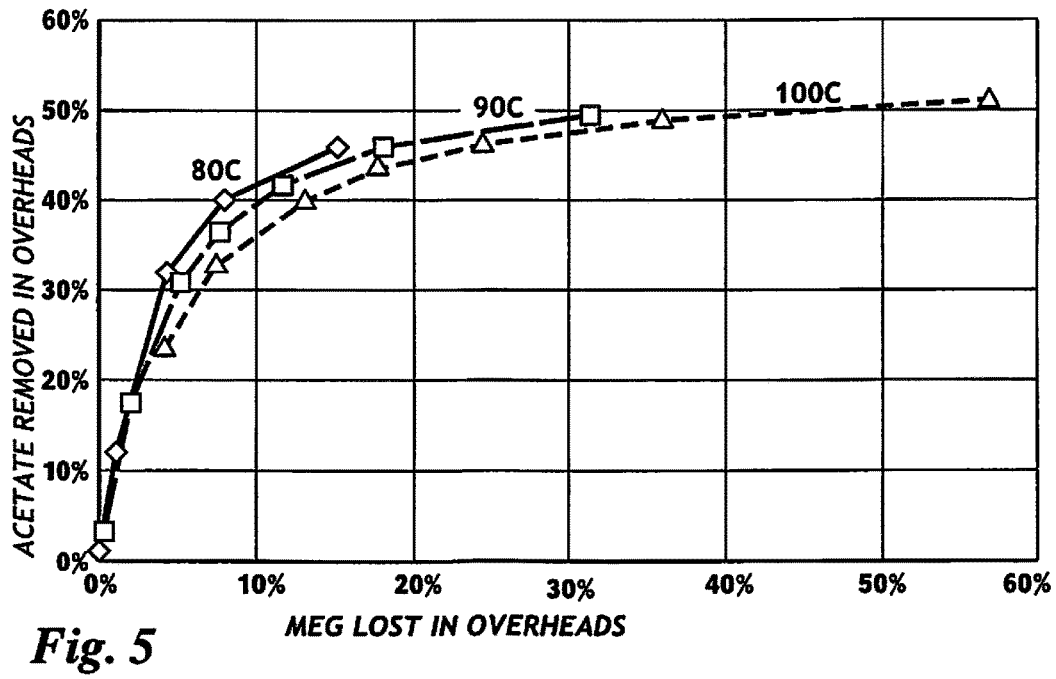
Figure 6:
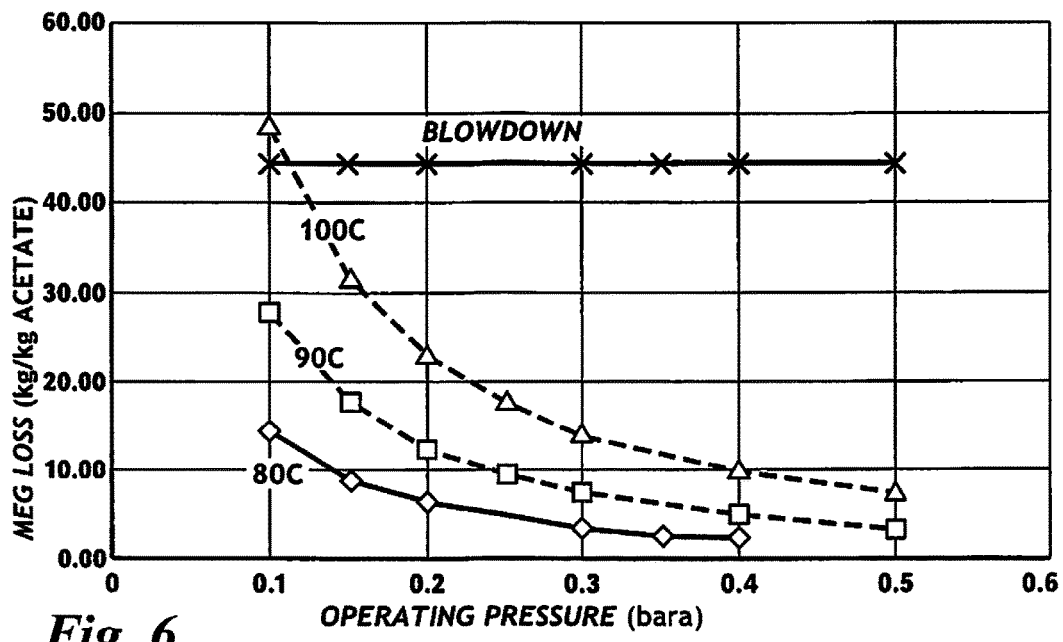

FIG. 5 plots acetate removal against MEG loss for three temperatures (80, 90 and 100° C.). Lower temperatures and low pressure are preferred to maximize acetate removal. FIG. 6 plots MEG loss as a function of acetate rejected from the MEG Loop. Using simple blowdown, 950 kg of MEG will be ejected with every 30 kg of sodium acetate (44 kg MEG per kg of acetate).

Figure 7:
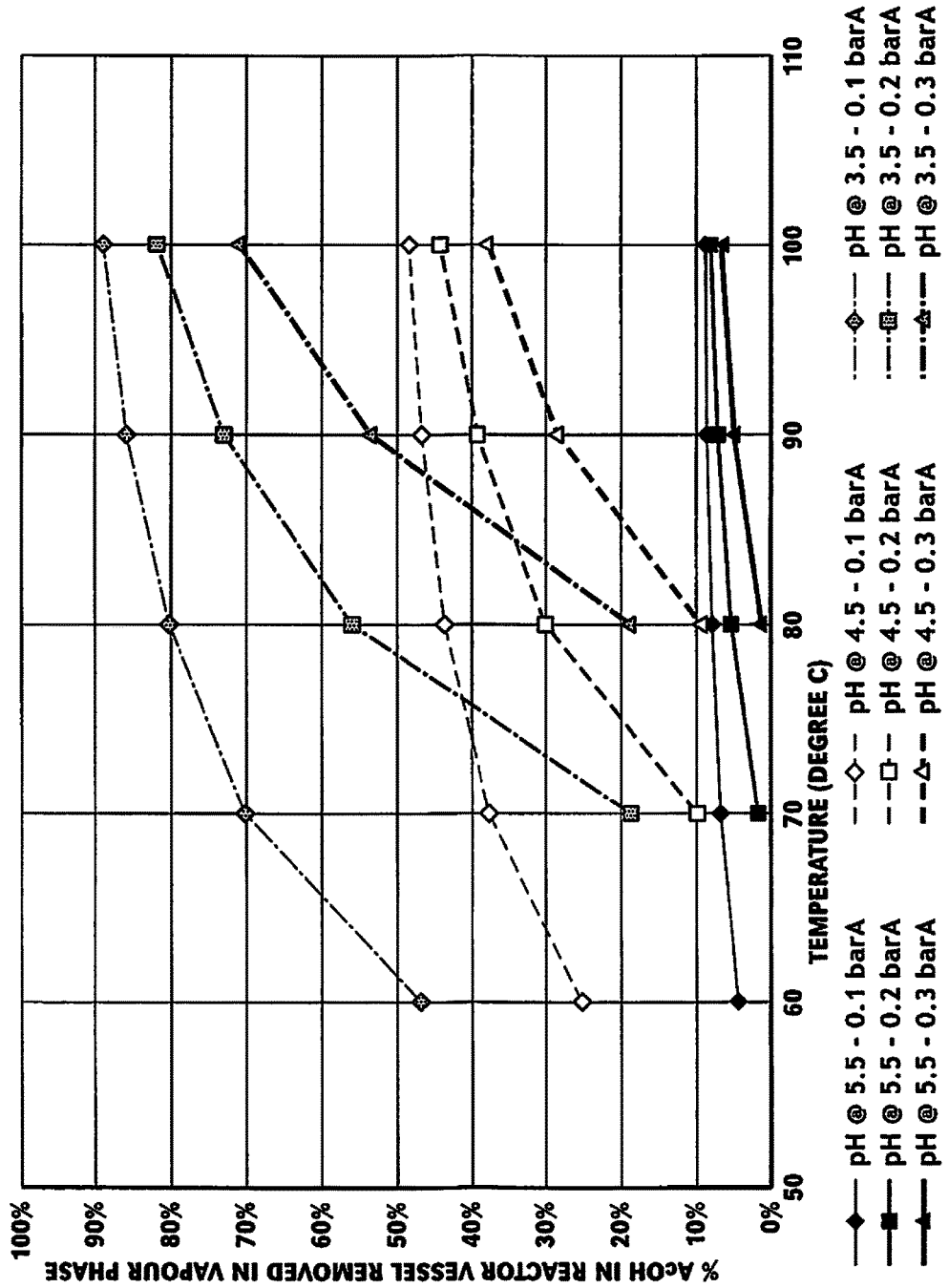

FIG. 7 plots acetate removal as a function of temperature and pressure for three initial pH conditions: 3.5, 4.5, 5.5). Acetate removal efficiency is increased as the starting solution pH is reduced. For a starting pH of 3.5, 89% of the acetate in the reaction vessel is removed in the overhead stream at 100° C. and 0.1 bara compared to 48.3% for an initial solution pH of 4.5 and 8.8% for an initial solution pH of 5.5.

Using the acidification/vaporization scheme practiced according to this invention can significantly reduce this MEG loss. At 80° C. and 0.15 bar, the simulation software predicts 73.8 kg of MEG in the overhead stream along with 8.75 kg of acetic acid (8.58 kg MEG per kg acetate). At 80° C. and 0.15 bar only 40% of the acetate is removed per batch with the acetate remaining in the liquid phase being routed back to the reclaimer for re-processing.

Experimental Results

Figure 8:
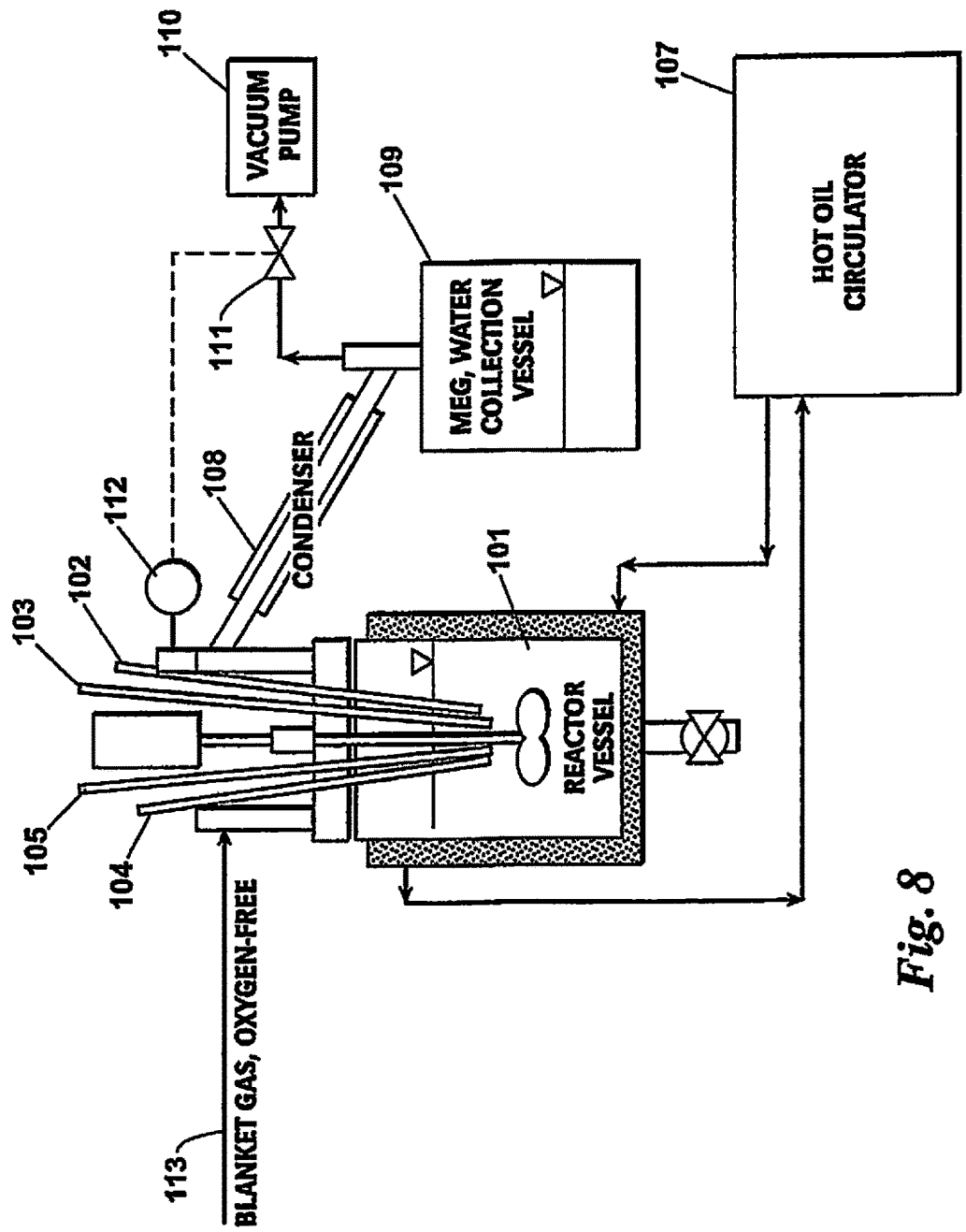
FIG. 8 is schematic of an apparatus used to test preferred embodiments of the system and process of this invention.

The apparatus used in the test is shown in FIG. 8. A double skinned 5L glass reactor vessel 101—fitted with a pH probe 102 (a Hamilton Polilyte Plus ARC 425), a dissolved oxygen probe 103 (Hamilton Oxygold G ARC 425), a redox probe 104 (Hamilton Polilyte Plus ORP ARC 425), an electrical conductivity probe 105 (Hamilton Conducell 4USF ARC PG425), and a stirrer 106—was heated by means of a hot oil circulator bath and heater 107. (Although probes 103, 104 and 105 were fitted to the reactor vessel 101, those probes were not used to collect data during the experiments.) The reactor vessel 101 was connected to a condenser 108 and a distillate collection vessel 109. The reactor vessel 101, condenser 108, and distillate collection vessel 109 were evacuated using a vacuum pump 110, a pressure control valve 111 and a pressure transducer 112. An oxygen-free nitrogen supply 113 was connected to the reactor vessel 101 to provide gas blanketing function.

A MEG-water-acetic acid solution was prepared in the reactor vessel 101 by adding 93 g of acetic acid (99-100% ex Sigma-Aldrich) to a mixture of monoethyleneglycol (1,737 g, Uninhibited CoolFlow MEG ex Hydra Technologies Limited, Fforestfach, Swansea SA5 4AJ, UK) and de-ionised water (1,710 g). The pH of this solution was measured as 2.61 at 23° C. The acetate content of the solution was calculated as 2.58 wt %.

The pH of the test mixture was elevated to 10.2 by addition of 100 g of anhydrous sodium carbonate (ex Sigma-Aldrich) and 1 g of sodium hydroxide pellets (ex Sigma-Aldrich). At this high pH, the acetic acid is converted to sodium acetate which is non-volatile and which would not be removed from the reaction vessel by elevating the temperature and reducing the operating pressure.

In conventional MEG loops the organic acids in the formation water and condensed water are usually present as the sodium salt:

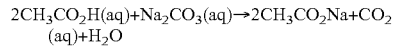

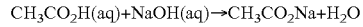

In order to effectively remove the dissolved acetate the pH of the solution was reduced from 10.2 to 3.5 by addition of 70 g of 37 wt % hydrochloric acid solution (Sigma-Aldrich). The pressure in the reactor vessel 101 was reduced to 0.15 barA and the temperature was raised to 80° C. The reactor vessel 101 was held at 0.15 barA/80° C. for approximately 3.3 hours.

The reactor vessel 101 was allowed to cool and the residue in the vessel 101 and the distillate collected in the MEG-water collection vessel 109 were weighed and analyzed. The results are shown in Table 1 below.

Table 1 shows that the MEG level in the reactor vessel 101 rises from 53.6 wt % to 93.7 wt % as the water component is removed in preference to the less volatile MEG at low pressure and elevated temperatures. Table 1 also shows that the acetate component in the reactor vessel 101 is also removed in preference to the MEG component and that the acetate content of the distillate (predominantly water) is higher (29,093 mg/L) than in the original reactor mixture (measured at 20,994 mg/L, calculated from starting composition at 25,396 mg/L).

TABLE 1

Analysis of Reactor and Distillate Vessel Contents

| | Inventory (g) | MEG by GC [Note 1] (wt %) | Estimated Density [Note 2] (g/L) | Acetate by IC [Note 3] (mg/L) | Acetate Calculated [Note 4] (g) |
|---|---|---|---|---|---|
| Reactor @ t = 0 | 3,781 | 53.6 | 1,065 | 20,964 | 75.49 |
| Reactor @ t = 3.33 hrs | 2,079 | 93.7 | 1,109 | 17,326 | 32.75 |
| Distillate @ t = 3.33 hrs | 1,580 | 6.7 | 1,006 | 29,093 | 45.69 |

[Note 1]:
MEG content measured by Gas Chromatography
[Note 2]:
Density estimated as a function of MEG:water:dissolved salt at 20° C.
[Note 3]:
Acetate content measured using Ion Chromatography
[Note 4]:
Acetate(g) = Acetate (mg/L) × Inventory (g)/Density (g/L)

Based on a total final acetate measurement of 78.44 g (32.75 g remaining in the reactor vessel 101 plus 45.69 g collected in the distillate), it is calculated that 58.3% in the acetate present as sodium acetate in the reactor vessel at pH=10.2 was removed as acetic acid by reducing pH to 3.5 then reducing the pressure to 0.15-0.17 barA and raising the temperature to 80° C.

Experimental results and predicted values from the OLI STREAM ANALYZER™ are shown in Table 2, below. The OLI model predicts 70% removal of acetate at 80° C./1.5 barA.

TABLE 2

Experimental acetate removal compared with simulated results

| | pH | TEMP degC. | PRESSURE barA | ACETATE REMOVED % |
|---|---|---|---|---|
| OLI Prediction | 3.50 | 80 | 0.15 | 70.0 |
| Experimental | 3.34-3.78 | 66-80 | 0.14-0.17 | 58.3 |

SUMMARY

The above preferred embodiments of a system and method made and practice according to this invention are not all possible embodiments. The claims listed below define the scope of the invention, including equivalents to the elements listed.

What is claimed:

1. A process for removal of organic carboxylates from a mono ethylene glycol ("MEG") stream, the process comprising:
   routing a MEG stream having organic carboxylates in solution to a reaction vessel;
   acidifying the MEG stream during its residence time within the reaction vessel to a pH of about 3.5 to about 5.5, the organic carboxylates remaining in solution as carboxylic acid; and
   removing in a vapor phase a carboxylic acid-rich overhead stream from the reaction vessel.

2. The process according to claim 1 further including the step of cooling the MEG stream being routed to the reaction vessel.

3. The process according to claim 1 further including the step of diluting the MEG stream being routed to the reaction vessel.

4. The process according to claim 1 further including the steps of cooling and diluting the MEG stream being routed to the reaction vessel to a lower % wt MEG and a lower temperature than an upstream % wt MEG and temperature of the MEG stream.

5. The process according to claim 4 wherein the raising alkalinity of said MEG stream step includes adding at least one of sodium carbonate, potassium carbonate, sodium hydroxide, and potassium hydroxide.

6. The process according to claim 4 wherein the lower % wt MEG is below 80 wt % MEG.

7. The process according to claim 6 wherein the lower % wt MEG is about 50 wt % MEG.

8. The process according to claim 4 wherein the lower temperature is a temperature in a range of 80° to 100° C.

9. The process according to claim 4 wherein the cooling and diluting the MEG stream step includes water.

10. The process according to claim 4 wherein the acidification of the cooled and diluted MEG stream occurs under a vacuum.

11. The process according to claim 1 wherein the MEG stream also includes calcium and wherein the reaction vessel includes an acetate removal mode and a calcium removal mode, the process further comprising the step of alternating the reaction vessel between the above mentioned modes, the pressure of the reaction vessel being greater during the calcium removal mode than during the acetate removal mode.

12. The process according to claim 1 wherein the reaction vessel is located downstream of a calcium removal vessel within a MEG recycle loop, the process further comprising a step of routing a bottom stream from the calcium removal vessel to the reaction vessel.

13. The process according to claim 1 further comprising a step of raising the alkalinity of the MEG stream prior to its residence time within the reaction vessel.

14. The process according to claim 1 wherein the MEG stream also includes calcium and further comprising the step of removing a calcium-rich bottom stream from the reaction vessel.

15. The process according to claim 1 wherein the reaction vessel is at a pressure in a range of 0.1 to 0.3 bar.

16. The process according to claim 1 wherein the acidifying step includes the addition of hydrochloric acid.

17. A process for removal of organic carboxylates from a mono ethylene glycol ("MEG") stream, the process comprising:
   acidifying the MEG stream during its residence time within a reaction vessel the MEG stream having organic carboxylates including at least organic acetates in solution and a lower wt % MEG and a lower temperature within the reaction vessel than upstream of the reaction vessel, the organic acetates remaining in solution during the residence time as acetic acid, the acidifying step resulting in the MEG stream having a pH in a range of about 3.5 to about 5.5; and
   removing when in vapor phase said acetic acid in a carboxylate-rich overhead stream from the reaction vessel.

18. The process of claim 17 wherein the acidification of the MEG stream occurs under sub-ambient pressure.

19. The process according to claim 18 wherein the sub-ambient pressure is a pressure in a range of 0.1 to 0.3 bar.

20. The process according to claim 17 wherein the acidifying step includes hydrochloric acid.

21. The process according to claim 20 wherein the reaction vessel is at a pressure in a range of between about 0.1 bar and about 0.3 bar.

22. The process according to claim 17 wherein the lower wt % MEG is below 80 wt % MEG.

23. The process according to claim 17 wherein the lower wt % MEG is about 50 wt % MEG.

24. The process according to claim 17 wherein the lower temperature is in a range of 80° to 100° C.

25. A process for removal of organic carboxylates and calcium from a mono ethylene glycol ("MEG") stream, the system comprising:
   routing the MEG stream to a reaction vessel;
   raising the alkalinity of the MEG stream to convert said organic carboxylates to carboxylate salt in solution and said calcium to calcium carbonate in solution;
   removing said calcium carbonate from the reaction vessel;
   acidifying the MEG stream in the reaction vessel to a pH about 3.5 to about 5.5, the carboxylate salt being converted to carboxylic acid; and,
   removing said carboxylic acid from the reaction vessel.

26. The process of claim 25 wherein solids are precipitated from the MEG stream after raising the alkalinity and the process includes the further step of removing said solids.

27. The process of claim 25 wherein the raising the alkalinity of the MEG stream step and the removing said calcium carbonate step occur prior to the acidifying of the MEG stream step and removing said carboxylic acid step.

28. The process of claim 25 wherein the acidifying of the MEG stream step and removing said carboxylic acid step occur prior to the raising the alkalinity of the MEG stream step and the removing said calcium carbonate step.

* * * * *